United States Patent [19]

Cameron

[11] 4,321,545
[45] Mar. 23, 1982

[54] CARBON DIOXIDE MEASUREMENT SYSTEM

[76] Inventor: James N. Cameron, P.O. Box 742, Port Aransas, Tex. 78373

[21] Appl. No.: 130,086

[22] Filed: Mar. 13, 1980

[51] Int. Cl.$^3$ ............................................. G01N 27/42
[52] U.S. Cl. .................................... 324/442; 324/439; 324/450
[58] Field of Search ............................... 324/439, 450

[56] References Cited

U.S. PATENT DOCUMENTS

| | | | |
|---|---|---|---|
| 2,795,756 | 6/1957 | Jacobson et al. | 324/450 |
| 3,527,571 | 9/1970 | Newberger | 324/450 |
| 3,874,850 | 4/1975 | Sorensen | 324/439 |
| 3,992,267 | 11/1976 | Oswin | 324/450 |
| 4,228,400 | 10/1980 | Bruckenstein | 324/450 |

*Primary Examiner*—Michael J. Tokar

[57] ABSTRACT

A method and apparatus wherein a sample of gas or fluid containing carbon dioxide in the form of dissolved carbon dioxide gas, bicarbonate ion, and/or carbonate ion is injected into an extraction chamber provided with an acid extracting fluid. A carbon dioxide-free gas stream is passed through the extraction chamber in order to carry the dissolved $CO_2$ gas formed from bicarbonate and carbonate ions, as well as that already present, onto a spiral absorbing column, wherein a dilute alkaline solution absorbs the $CO_2$ with a resulting change in electrical conductivity of the alkaline solution. The system disclosed provides electrical means for measuring the conductivity difference thus produced, means for conversion of this difference to an appropriately coded electrical signal, and means for providing a direct display of the sample concentration. Means are provided for indicating when a sample is being processed by the apparatus, and for holding the displayed concentration until manually re-set. Two types of extraction chambers are disclosed, one for gas and non-foaming liquids, and a second for foaming liquids such as blood. The method and apparatus is suitable for use with samples containing as little as 20 nano-Moles ($10^{-9}$ Moles) of carbon dioxide in all forms.

2 Claims, 4 Drawing Figures

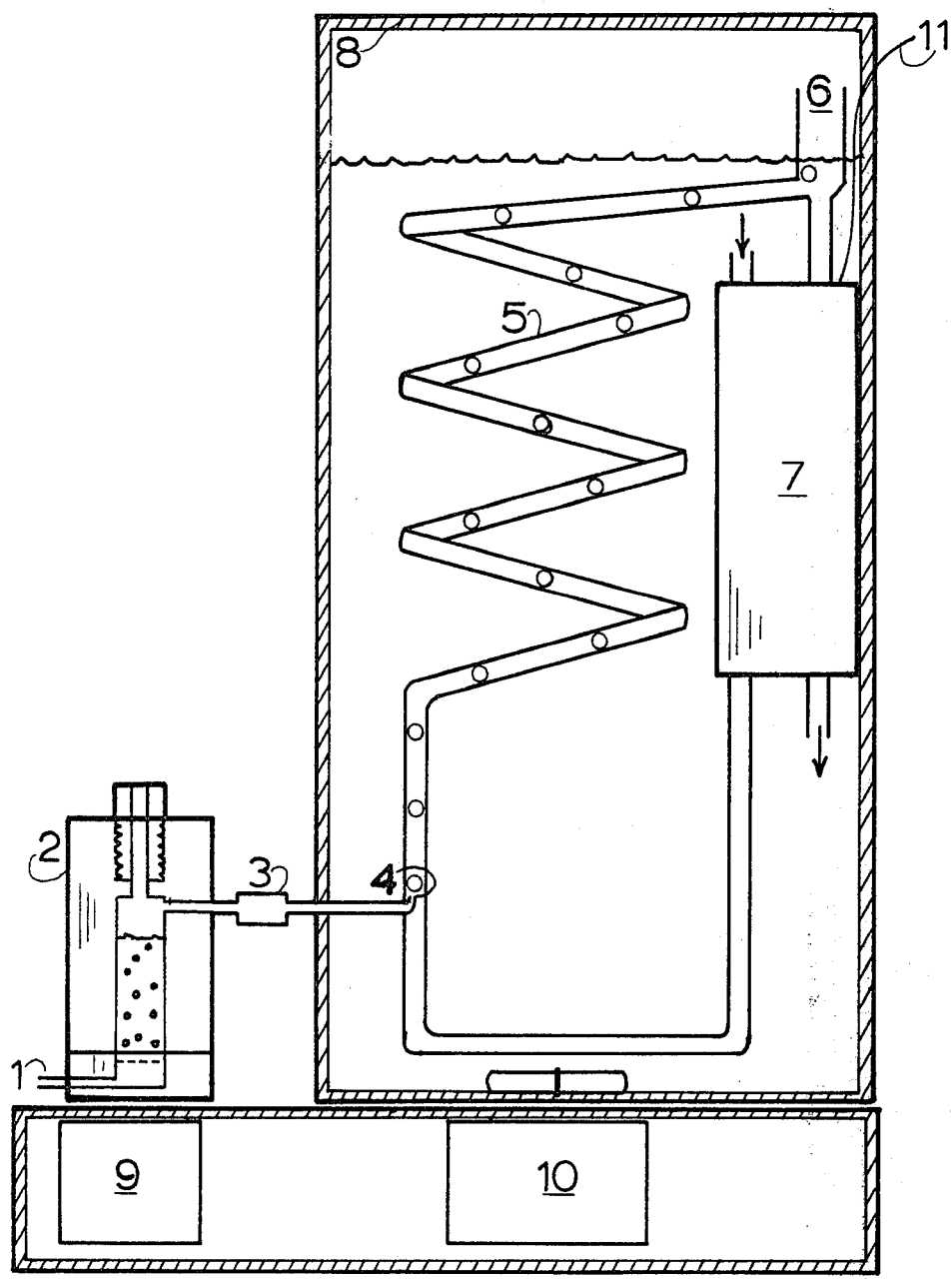
- FIG. 1 -

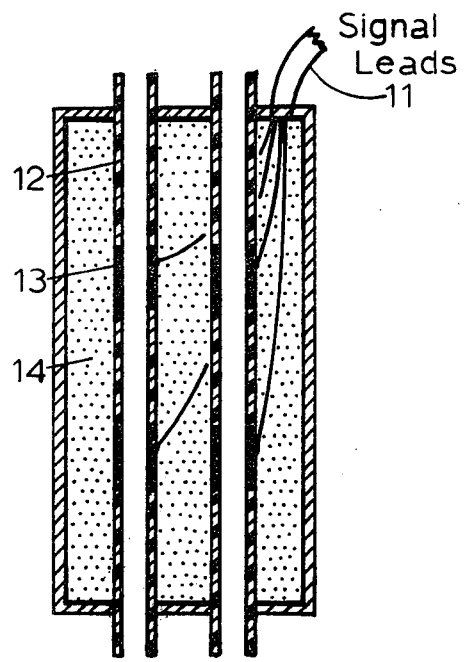 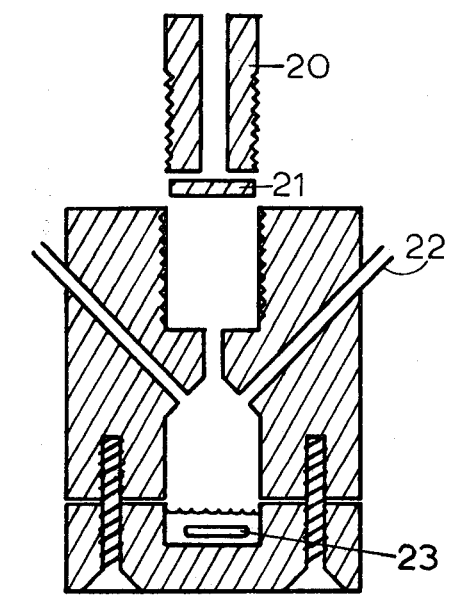
Detector
-FIG. 2-
Alternate Extraction Chamber
- FIG. 3 -

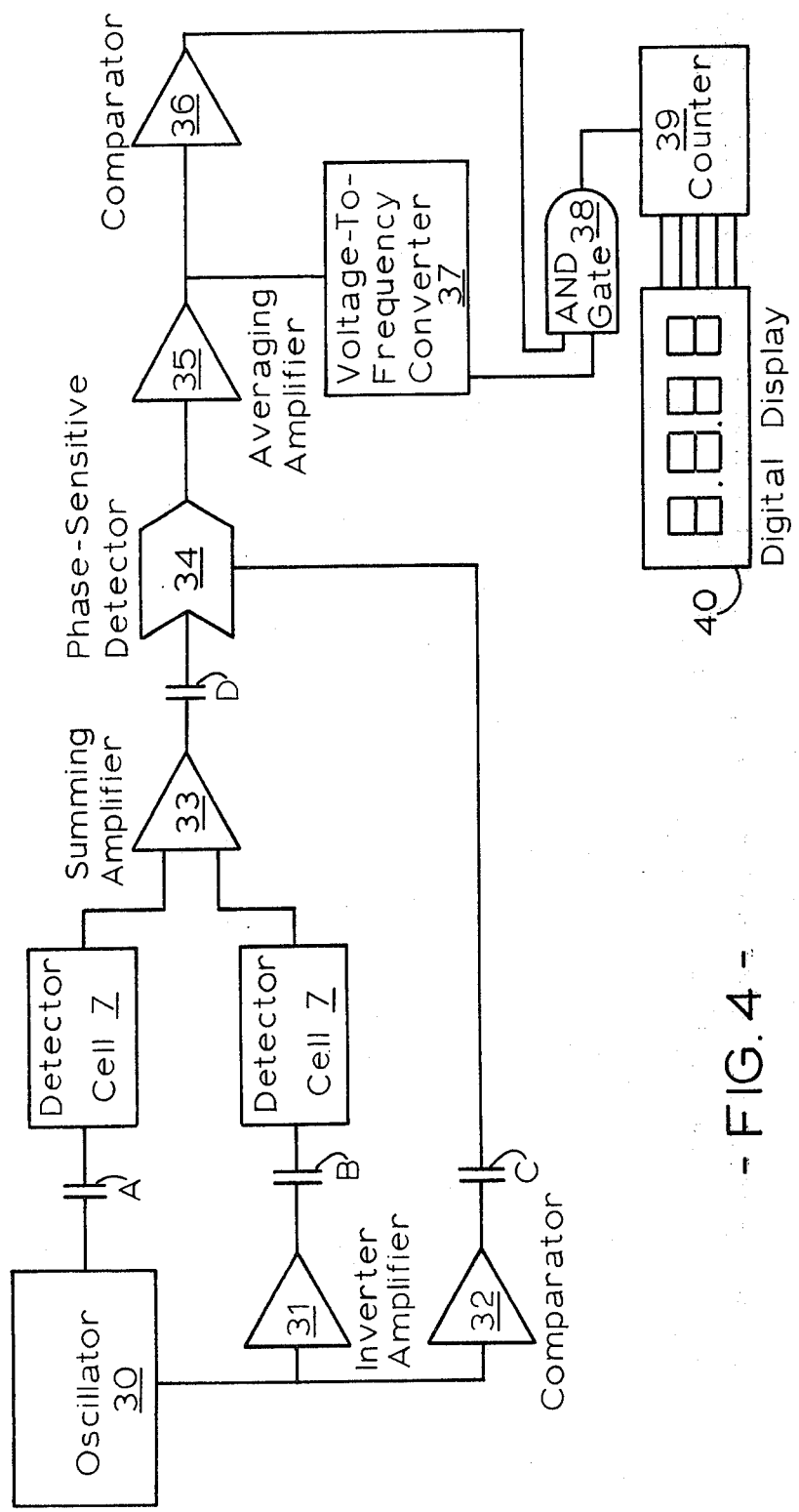
-FIG. 4-

CARBON DIOXIDE MEASUREMENT SYSTEM

BACKGROUND

The measurement of the total concentration of all forms of $CO_2$ in fluid samples, i.e. dissolved gas, carbonic acid, bicarbonate ions, and carbonate ions, is generally difficult to accomplish with methods currently known and in use. All these forms exist in chemical equilibrium in aqueous solutions, and methods of measurement depend either on conversion of all forms to a single one that can be measured, or upon measurement of two or more parameters of the equilibrium system combined with calculation of the rest from known equilibrium constants. The most common method in use today consists of measuring the pH of the solution, and the partial pressure of dissolved $CO_2$ gas with a Severinghaus-type electrode, combined with various calculation routines or graphical nomograms used to estimate the remaining parameters. This method has a number of problems: the measurement of pH is a logarithmic one, so small errors may cause relatively large errors in the calculation of other parameters; the $CO_2$ electrodes are subject to drift, have a very slow response at very low partial pressures, and have an unacceptable loss of sensitivity and response time at temperatures much below human body temperature.

A second method no longer used commonly depended on conversion of all forms of $CO_2$ to $CO_2$ gas by acidification, followed by measurement of the gas evolved in a manometric apparatus. This method, too, is subject to numerous errors, principally volumetric errors in measurement of the several reagents employed, temperature fluctuations, and mercury manometer manipulation errors. In addition, the method is tedious and time-consuming, requires considerable skill, and is little used today.

A third method developed by this petitioner (not patented) depends upon acidification of the fluid sample to convert all combined forms of $CO_2$ to dissolved $CO_2$ gas, as in the method just outlined above, but the acidification is carried out in a small closed chamber containing a $CO_2$ electrode. The increase in partial pressure in this small volume upon acidification of an unknown sample is compared with the partial pressure increase resulting from acidification of a known standard in order to calculate the concentration of the unknown. This method suffers many of the same problems inherent in the others, especially the inherent response and drift characteristics of the $CO_2$ electrodes.

Conductivity change in alkaline solutions upon absorption of $CO_2$ has been employed to measure the $CO_2$ in gas samples, but the principal has not been applied in a direct way to small fluid samples, and the temperature dependence of the conductivity change has not been dealt with effectively. There is clearly a need for a new method, or improvements in present methods for making a simple, direct measurement of the total of all forms of $CO_2$ in samples of liquids.

SUMMARY OF THE INVENTION

The present inventor has discovered that a system can be constructed which provides high sensitivity and stability, and provides the convenience of direct readout of sample concentration by employing an acid extraction chamber, an alkaline absorbing column, a differential conductivity detection system, and electrical circuitry for measurement, amplification, and display of the conductivity change resulting from injection of a fluid sample. The method and apparatus disclosed enable quick and convenient analysis of samples containing as little as 20 nano-Moles ($20 \times 10^{-9}$ Moles) of $CO_2$ in all its various forms (e.g. 20 micro-Liters of a sample containing 1 milli-Mole per Liter), can be employed with samples as small as 5 micro-Liters, and require no other laboratory equipment. The method and apparatus have been applied, but are not limited to analysis of natural surface waters, sea water, blood of various animals, urine samples from various animals, culture media, and gas samples.

This invention, together with the advantages thereof, may best be understood by reference to the following description taken in connection with the accompanying drawings.

BRIEF DESCRIPTION OF THE DRAWINGS

FIG. 1 is a functional block diagram of the mechanical portions of the apparatus showing the path of gas flow through the extraction chamber, the absorbing column, and the bath.

FIG. 2 is a detailed section view of the detector.

FIG. 3 is a detailed section view of one type of extraction chamber employed in the apparatus.

FIG. 4 is a functional schematic of the electronic circuitry employed for signal detection, amplification, and digital display and control.

DETAILED DESCRIPTION

Analysis of the total carbon dioxide contained in a sample consists of three principal steps: injection of the sample into an acid extraction fluid wherein the sample is wholly converted to $CO_2$ gas and removed by a $CO_2$-free gas stream; absorption of the $CO_2$ from the carrier gas stream in an alkaline solution passing through a spiral absorbing column; and, finally, detection of the absorbed $CO_2$ by a conductivity difference in the alkaline solution, this last accomplished by the detector and its associated electronic circuitry. Referring to FIG. 1, the mechanical portions of the apparatus designed to carry out this process are depicted. The $CO_2$-free gas stream enters the extraction chamber through an inlet (1), bubbles through the acid extraction medium via a fritted glass disc or similar provision in the bottom of the chamber (2), then passes out of the extraction chamber. Samples are introduced through the top of the extraction chamber (2) via a septum or similar closure device. Upon leaving the extraction chamber, the carrier gas passes through an aerosol trap (3) which prevents fine acid bubbles from being carried onto the alkaline absorbing column, and then enters the bath (8) and the absorbing column (5) via a restricted inlet (4). As the bubbles rise from the restricted inlet (4), they cause the fluid in the absorbing column (5) to circulate in the following fashion: fluid first enters one side of the detector cell (7) as shown by the arrow in FIG. 1, flows down and around past the restricted inlet (4), and upon reaching the top of the absorbing column (5), flows down again through the other side of the detector (7). Bubbles are allowed to escape from the top of the absorbing column (6) after their $CO_2$ has been absorbed during their passage up the spiral. The bath (8) is of fairly large volume, 8 to 10 liters having been found satisfactory in examples that have been constructed, and is kept well mixed by a magnetic stirrer (10). This ensures that the composition of the bath fluid is nearly constant over time, changing only very slowly as its absorbing capacity is used up, and also ensures that temperature variations are damped out by the large thermal inertia of the fluid.

When a sample containing $CO_2$ is introduced into the extraction chamber, the equilibrium existing between $CO_2$ gas, carbonic acid, bicarbonate ions, and carbonate is rapidly displaced to favor $CO_2$ gas almost exclusively. At the same time, the $CO_2$-free gas stream (nitrogen has been found to be suitable) rapidly strips the $CO_2$ out of solution, since the gas and liquid phases tend to come to equilibrium, and the gas phase is constantly being replaced. There are no interfering substances in most natural fluids; other gases, such as oxygen and nitrogen, may be removed from the sample in the extraction chamber, due to equilibration with the nitrogen stream, but they do not react with the dilute alkali, and do not register as a conductivity difference. Other acid gases, such as $SO_3$, may interfere with the procedure in certain solutions and gas samples, such as stack gas. The method and apparatus may also be adapted and used to measure $SO_3$ or other "acid" gases. Gas samples are injected into the apparatus in the same way as liquids, but no acid is required; they are simply carried onto the absorbing column (5) by the carrier gas stream.

For some samples, such as blood, the extraction chamber shown in FIG. 1 is not suitable, since the bubbling of the carrier gas stream up through the acid and sample causes excessive foaming, mostly due to proteins. For these samples, the extraction chamber shown in FIG. 3 is suitable. It is similar to the one shown in FIG. 1, except that the carrier gas stream enters and leaves by tubes (22) above the liquid level, passing over the rapidly stirred acid-sample mixture. The mixing is achieved by a small magnet (23) coupled with another magnetic stirrer (9, FIG. 1); the sample is injected through a septum (21) held in place by a collar (20), as in the chamber shown in FIG. 1.

The detector employed is shown in section view in FIG. 2. It consists of two tubes, each forming one cell of the detector. Each tube is made up of non-conducting material (12) such as a plastic, with two separated portions of a conducting material (13) that form the actual electrodes. One signal lead (11) is connected to each electrode (13); i.e. there are two from each tube, or cell, and a total of four (11) that go to the electronics. The whole of the detector assembly is encapsulated in a non-conducting material (14) in a non-conductive housing.

The electronic circuitry employed along with the extraction, absorption, and detector components described above is shown in FIG. 4. In order to avoid capacitance effects, polarization effects, and resulting electrode corrosion and performance degradation in the detector, an oscillator is employed to provide a low-current AC signal to the detector cells. A variety of oscillators would be suitable, but the present applicant has had successful applications of an amplitude-stabilized Wien bridge type (30). The oscillator signal is applied to one detector cell through an inter-stage coupling capacitor (A), and to the other through an inverting amplifier (31) and inter-stage coupling capacitor (B), so that the two signals are 180 degrees out of phase. The resultant net current is amplified by a summing amplifier (33), and then connected to a phase sensitive detector (34) via an inter-stage coupling capacitor (D). The phase-sensitive detector (34) employs a chopping signal generated by a comparator (32) connected to the oscillator (30), the comparator being isolated from the phase-sensitive detector by a capacitor (C). The function of the phase-sensitive detector is to remove out-of-phase components of the AC current signal generated by the summing amplifier (33), thus presenting an output proportional to resistive conductivity only, and removing capacitance effects. The signal from the phase-sensitive detector (34) is amplified and smoothed by an integrating (averaging) amplifier (35). This smoothed analog signal is adjusted to zero when no sample is being processed by adjusting the gain of the inverting amplifier (31). The remainder of the circuitry is designed to convert the analog signal to digital form, and to switch the digital circuitry on and off automatically as a sample is processed.

The analog output signal is fed to a voltage-to-frequency converter (37) that generates a train of pulses proportional to the voltage. Injection of a sample causes a peak to appear at the output of the analog averaging amplifier (35), and counting of pulses from the voltage-to-frequency converter (37) over the length of the peak appearance cycle provides an intergrated measurement of the peak signal. The apparatus is provided with a re-set which sets the display to zero at the beginning of sample processing. When the analog signal rises to a pre-set threshold above the zero baseline, it triggers a comparator (36) that enables pulses from the voltage-to-frequency converter (37) to pass through an AND gate (38), and thence to the counters (39) and display (40). In order to scale the number of pulses counted in such a way as to have the display show the sample concentration in convenient units, either the gain of the averaging amplifier (35) may be made adjustable, a voltage divider network interposed between that amplifier (35) and the voltage-to-frequency converter (37), or various dividing counters interposed between the voltage-to-frequency converter (37) and the counters (39); or a combination of all these methods may be employed.

When the signal from processing of a sample has returned to a pre-set level just above the zero baseline, the comparator (36) shuts off, preventing any further pulses from passing the AND gate, and freezing the value in the display. The comparator (36) has a slight hysteresis built in to prevent false triggering and noise-generated pulses. Indicator lights may also be attached to the output of the comparator (36) through switching transistors in order to have an indication of when a sample is being processed, and when it is finished.

In order to actually operate the device, the chamber is first filled with a good quality distilled water (1 micromho conductance or less is best), to which sodium hydroxide is added to bring the concentration to 0.001 N, although concentrations above or below that may also be satisfactory. Several minutes are then allowed with stirring of the bath to ensure complete mixing. The carrier gas flow is then started and adjusted so that the bubbles take about 30 seconds to travel from the restricted inlet (4) to the top of the column (6). A constant gas flow rate is necessary to obtain reproducible results. After this initial adjustment and stabilization, the electronics are adjusted to zero with no sample present. The machine is then calibrated by injecting a sample having a known total $CO_2$ concentration, and adjusting the electronics to give the correct direct concentration on the digital display. This may require two or three repetitions. Thereafter, samples to be analyzed are simply injected, the display re-set to zero, and after a time interval ranging from one to three minutes, the actual sample concentration is displayed.

One such actual device that has been successfully built and tested employed integrated circuit dual operation amplifiers (LM747) for portions of the oscillator (30), the inverter (31), the summing amplifier (33), and the phase-sensitive detector (34); another integrated circuit operation amplifier (LM741) for comparators (32) and (33); an integrated circuit bi-FET input operation amplifier (RCA CA3140S) for the averaging amplifier (35); a medium scale integrated circuit (Analog Devices AD537KD) as a voltage-to-frequency converter; various TTL logic devices for the AND gate (38) and counters (39); a voltage divider network between averaging amplifier (35) and the VFC (37); and various resistors and capacitors needed for input bias, interstage coupling, zero offset, etc.

While one particular embodiment of the invention has been shown and described, it will be obvious to those skilled in the art that changes and modifications may be made without departing from the invention in its broader aspects and therefore, the aim of the appended claims is to cover all such changes and modifications as fall within the true scope and spirit of the invention.

I claim:

1. A method of obtaining consistent and reproducible results from a $CO_2$ measuring system whose detection is based on the principal of electrical conductivity change in an alkaline solution, wherein temperature fluctuations, small sample problems, and foaming of liquids are prone to cause error, comprising the steps of:
    (a) injecting a sample into an extraction chamber, wherein
    (b) an acid solution is employed to convert bicarbonate ion, carbonate ion, and carbonic acid, the usual chemical formulae for which are $HCO_3^-$, $CO_3^{2-}$, and $H_2CO_3$, respectively, to dissolved $CO_2$ gas,
    (c) removal of the $CO_2$ from the extraction chamber by a carrier gas stream containing no $CO_2$,
    (d) employing the carrier gas stream to conduct the removed $CO_2$ onto a column wherein it is brought into contact with an alkaline solution, which re-absorbs $CO_2$,
    (e) employing the same carrier gas stream further to circulate the alkaline absorbing fluid first through one cell of a detector, then through a second cell of a detector after absorption of the $CO_2$ has occurred,
    (f) employing analog and digital circuitry to provide an automatically switched counting period, at the end of which the sample concentration is directly displayed.

2. Apparatus for the application of the method of conductivity difference measurement to the measurement of the total carbon dioxide content of a gas or fluid, wherein an acid medium is employed to remove all $CO_2$ from a solution into a carrier gas stream, and an alkaline absorbing fluid is used to re-absorb the $CO_2$ from the carrier gas stream and thus produce an electrical conductivity difference in the alkaline absorbing fluid, comprising:
    (a) an integrated piece of apparatus for conducting the entire process following the single step of injecting a sample,
    (b) the combination of acid extraction chamber and alkaline absorber column and bath driven by a carrier gas stream, this stream providing the circulating action in both extraction chamber and alkaline absorber column and detectors,
    (c) the combination of AC oscillator circuitry for detecting the difference in electrical conductivity produced as a result of a sample being processed, and digital circuitry to start and stop integration of the signal from a sample automatically and to scale the intergrated output in a visual display so as to provide a direct measurement of the concentration in the sample,
    (d) the provision of extraction chambers to be used with gas, non-foaming liquids, and with foaming liquids such as blood.

* * * * *